United States Patent [19]

Burkholder

[11] 4,230,890

[45] Oct. 28, 1980

[54] METHOD OF RECOVERING DIALKYLBENZENE DIHYDROPEROXIDE

[75] Inventor: Ward J. Burkholder, Baton Rouge, La.

[73] Assignee: The Goodyear Tire & Rubber Company, Akron, Ohio

[21] Appl. No.: 926,139

[22] Filed: Jul. 19, 1978

Related U.S. Application Data

[63] Continuation-in-part of Ser. No. 34,634, May 4, 1970, abandoned.

[51] Int. Cl.$^3$ .......................................... C07G 179/035
[52] U.S. Cl. .................................................... 568/576
[58] Field of Search ...................... 260/610 A, 610 B; 568/576, 562

[56] References Cited

U.S. PATENT DOCUMENTS 2,812,357  11/1957  Webster ........................... 260/610 A Primary Examiner—Werren B. Lone
Attorney, Agent, or Firm—C. James Bushman; J. Y. Clowney

[57] ABSTRACT

Separation of diisopropylbenzene dihydroperoxide from a diisopropylbenzene oxidation reaction mixture by treating the reaction mixture with concentrated alkali metal hydroxide and recovering the alkali metal salt of diisopropylbenzene dihydroperoxide in high purity and good yield, and subsequently converting the salt to diisopropylbenzene dihydroperoxide.

16 Claims, No Drawings

METHOD OF RECOVERING DIALKYLBENZENE DIHYDROPEROXIDE

CROSS REFERENCE TO RELATED APPLICATION

This is a continuation-in-part of my prior co-pending application Ser. No. 34, 634, filed May 4, 1970, now abandoned.

BACKGROUND OF THE INVENTION

The prior art teaches the production of meta- and para-diisopropylbenzene dihydroperoxide by the liquid phase oxidation of meta- and para-diisopropylbenzene with molecular oxygen in the presence of alkaline materials.

This oxidation reaction yields an oxidate which contains dihydroperoxide, monohydroperoxide, unreacted diisopropylbenzene, (2-hydroperoxy-2-propyl) phenyldimethylcarbinol, and small amounts of other reaction by-products. For this discussion, the (2-hydroperoxy-2-propyl) phenyldimethylcarbinol will be referred to as carbinol hydroperoxide and will be prefaced with p- or m- to indicate the para- or meta- isomer thereof. The proportion of monohydroperoxide relative to dihydroperoxide is large in the oxidate, there typically being 2 to 3 times as much monohydroperoxide as dihydroperoxide. Unreacted diisopropylbenzene is also present in large amounts in the oxidate product when dihydroperoxide is the desired product, since if the oxidation is carried too far toward completion the efficiency of dihydroperoxide production decreases as by-products increase. Therefore, the oxidation is typically carried to 30 to 40% completion based upon all hydroperoxide calculated as dihydroperoxide. The carbinol hydroperoxide is a by-product of the oxidation reaction and typically exists in an amount equal to about 20% of the dihydroperoxide present in the oxidate. The other oxidation by-products are present in small amounts, typically amounting to a few percent of the total oxidate.

The dihydroperoxide, when it is the desired product, has heretofore been recovered from the oxidate by extraction techniques, for example, with dilute aqueous solutions of alkali metal hydroxides of from about 1 to about 15% concentrations. Although the dihydroperoxide is extracted from most of the oxidate materials by the use of dilute aqueous alkali metal hydroxide solutions, the dihydroperoxide is not separated from the carbinol hydroperoxide. If it is required to recover the dihydroperoxide in substantial purity, then further measures must be taken to separate it from the carbinol hydroperoxide, for instance by further extraction from an organic solution with concentrated solutions of alkali metal hydroxides as described in U.S. Pat. No. 2,812,357. When the dihydroperoxide is so purified, employing concentrated solutions of alkali metal hydroperoxide, the dihydroperoxide is recovered as a solid alkali metal salt of the dihydroperoxide.

One method of regenerating the dihydroperoxide from its alkali metal salt is be treating a mixture of the salt of the dihydroperoxide in water with a weak acid. The weak acid reacts with the salt to form the dihydroperoxide, which is insoluble in water, and the alkali metal salt of the acid. The dihydroperoxide separates from the water phase and may be conveniently recovered by a physical separation means, such as decantation, filtration, centrifugation, etc. The amount of water present should be sufficient to dissolve the alkali metal salts of the acid which result from the acid treatment. The dihydroperoxide recovered by this method will be wet with the water solution of the salt. Any residual amount of the salt may be conveniently removed from the dihydroperoxide by washing the dihydroperoxide with water or with other wash materials in which the dihydroperoxide is relatively insoluble.

Any weakly acidic material may be used in this method of recovering dihydroperoxide from its alkali metal salt. The acids which may be employed include $CO_2$, acetic acid, other carboxylic acids, and dilute mineral acids. The preferred acid is $CO_2$ as it does not react to degrade the dihydroperoxide and is economical to use. The stronger acids, particularly the mineral acids, will react with the dihydroperoxides and destroy them unless the acids are carefully diluted. Such a reaction by the acid will decrease the dihydroperoxide yield and purity.

Another method of recovering the dialkylbenzene dihydroperoxide from its alkali metal salt is to dissolve the alkali metal salt in water to form a dilute aqueous solution. This aqueous solution is treated in an extraction process with a water-insoluble extraction liquid selected from the group comprising aliphatic ketones, aliphatic ethers, aliphatic alcohols and chlorinated aliphatic hydrocarbons, at a temperature of from 70° to 100° C. and in a ratio of extraction component to alkali phase of 0.2–5:1 and thereby extract the dihydroperoxide from the aqueous alkali phase. The dihydroperoxide may be recovered free of the organic solvent by vaporizing such solvent, thus yielding a crystalline hydroperoxide product. This method of recovering dialkylbenzene dihydroperoxide from its alkali metal salt is described in more detail in U.S. Pat. No. 3,190,923.

The dihydroperoxide, on recovery from the oxidate, is useful in the production of dihydric phenols and carbonyl compounds. For instance, the para-diisopropylbenzene dihydroperoxide can be rearranged, in the presence of an acid catalyst, to form hydroquinone and acetone, and the meta-diisopropylbenzene dihydroperoxide can be rearranged in the presence of an acid catalyst to form resorcinol and acetone.

From the point of view of producing hydroquinone and resorcinol with a minimum amount of contaminants and side reaction products, it is desirable to provide a substantially pure dihydroperoxide to the rearrangement reaction. For instance, any monohydroperoxide will rearrange to form isopropylphenol, which is a contaminant, and carbinol hydroperoxide will rearrange to form (2-hydroxy-2-propyl) phenol which is a contaminant, and which may dehydrate in the presence of the acid catalyst to form isopropenylphenol and, in either case, will tend to condense with the dihydric phenol to form a side reaction product and thereby reduce the yield of desired dihydric phenols. A dihydroperoxide of substantial purity may be easily recovered from a substantially pure metal salt of dihydroperoxide and its recovery in substantial purity and good yield from an oxidate is a first step toward the production of hydroquinone and resorcinol. The alkali metal salts of the dihydroperoxides are also useful as polymerization initiators for emulsion polymerizations.

SUMMARY OF THE INVENTION

It has been found that the alkali metal salts of meta- and/or para-diisopropylbenzene dihydroperoxide can be selectively precipitated, using concentrated alkali metal hydroxide solutions, in substantial purity and in good yield directly, from the oxidate mixture resulting from the oxidation of meta- and/or para-diisopropylbenzene, thereby providing an attractive method for separation of the dihydroperoxides from the oxidation products. These oxidate mixtures may contain monohydroperoxide in an amount up to about 2 to 3 times the amount of dihydroperoxide and the oxidate mixture may contain substantial amounts of carbinol hydroperoxide up to about 20% to 30% of the amount of dihydroperoxide present in the oxidate mixture. This method has the advantage that the alkali metal salt of the dihydroperoxide is recovered in good yield and substantial purity from the oxidate mixture by a single solid liquid separation step. The prior art (U.S. Pat. Nos. 2,527,640; 2,715,646) suggests that the monohydroperoxide salt will precipitate along with the dihydroperoxide salt when the oxidate is treated with concentrated alkali metal hydroxide solutions. I have found that by following the method of this invention only the dihydroperoxide salt is precipitated.

According to the present invention, the production of the alkali metal salt of dihydroperoxide in substantial purity and in good yield from the oxidate mixture resulting from the oxidation of diisopropylbenzene is obtained. The process comprises treating the oxidate mixture with an amount of water-immiscible solvent sufficient to reduce the viscosity of the oxidate and to keep the monohydroperoxide and carbinol hydroperoxide in solution; treating this mixture of oxidate and solvent with an aqueous NaOH solution of a concentration of about 50% or more in such an amount that a major amount of the dihydroperoxide is precipitated as its alkali metal salt, then recovering this salt from the remaining liquid by a convenient solid-liquid separation means and, finally, reconverting the dihydroperoxide salt to the dihydroperoxide. Alternatively, a portion of the organic solvent which is to be added to the oxidate may be reserved and this part may be used to wash the solid alkali metal salt of the dihydroperoxide. Such a wash will help remove the liquid oxidate materials which may be entrained in the solid salt.

DESCRIPTION OF THE PREFERRED EMBODIMENTS

The process of this invention is advantageously used for the separation and purification of para- and meta-diisopropylbenzene dihydroperoxide from the oxidate mixture produced by the liquid phase oxidation of the corresponding diisopropylbenzene at elevated temperatures with molecular oxygen in the presence of alkaline materials. Such an oxidate mixture typically consists of dihydroperoxide in a minor amount, monohydroperoxide in an amount of about 2 to about 3 times greater than the amount of dihydroperoxide, carbinol hydroperoxide in amounts of about 1/5 to about Ω the amount of dihydroperoxide, alkaline material in an amount of from about 0.5 to 15% of the total oxidate mixture, and various other oxidation reaction products in an amount not greater than a few percent of the total oxidate mixture which will vary according to the level of oxidation achieved in the oxidation reaction. Typically, the oxidation reaction will be carried to between about 30% and about 40% completion, calculated upon the basis that all the hydroperoxides are dihydroperoxides.

The water insoluble organic solvent which is added to the oxidate mixture according to the process of this invention may be chosen from a wide variety of organic solvents. The purposes of the organic solvent are to reduce the viscosity of the mixture which results when the alkali metal hydroxide solution is added to the oxidate material, and to maintain the monohydroperoxide and carbinol hydroperoxide in solution. If such solvent is not added, the oxidate-alkali metal hydroxide mixture becomes a thick, viscous mixture which does not readily filter. The properties which the organic solvent must necessarily possess in order to fulfill the requirements of this invention are that it is: substantially insoluble in water; soluble, in the proportion used, with the liquid oxidate material; not a solvent for the solid alkali metal salts of dialkylbenzene dihydroperoxides; not reactive, under processing conditions, with either the oxidate materials or the alkali metal hydroxide; will impart a viscosity lowering effect when a sufficient amount is added to the oxidate material. Other properties which this organic solvent should possess, although they are not critical to this invention, are: a boiling point sufficiently low to allow easy recovery of the organic solvent from the liquid oxidate materials which remain after the alkali metal salts of the dihydroperoxide are removed, a reasonable range of boiling points, preferably being between about 60° C. and 100° C.; and substantially refractory to oxidation by molecular oxygen under the conditions prevailing in the dialkylbenzene oxidation reaction in the case where some of the organic solvent may be recycled to the oxidation along with unreacted dialkylbenzene and monohydroperoxide. Examples of suitable organic solvents include benzene; liquid monoalkylbenzenes such as toluene, ethylbenzene, cumene; liquid dialkylbenzenes such as xylene, diisopropylbenzenes, diethylbenzenes; $C_3$–$C_{12}$ aliphatic hydrocarbons such as butane, hexane, heptane, decane; chlorinated aromatic hydrocarbons such as chlorobenzene and dichlorobenzene and mixtures thereof. Particularly preferred are benzene and normal aliphatic $C_3$–$C_{12}$ hydrocarbons. It will be appreciated that when low boiling point solvents, e.g. $C_3$–$C_4$ aliphatic hydrocarbons are employed, elevated pressures and/or decreased temperatures must be employed in order to maintain them in the liquid state. Benzene is the solvent of choice as it fulfills the necessary requirements and also possesses the noncritical, desirable properties enumerated above. The amount of organic solvent which may be used may be varied over a wide range. For instance, the volume/volume ratio of organic solvent to oxidate material may be varied from about 0.1 to about 6/1, depending upon the oxidation level of the oxidate material and upon the type of solid-liquid separation means to be employed. In the case of the preferred solvent, benzene, where the oxidation level of the oxidate is in the range of about 30% to about 40% (all hydroperoxide calculated as dihydroperoxide) and where ordinary solid-liquid separation techniques, such as light vacuum filtration, are employed, the preferred volume ratio of benzene to oxidate is from about 0.1/1 to 2/1.

The alkali metal hydroxide used in this invention may be selected from sodium hydroxide and potassium hydroxide, although sodium hydroxide is preferred from the cost standpoint. Preferably the alkali metal hydroxide is added as an aqueous solution having a concentration from in excess of 40%, especially in excess of 50%, to about 100% NaOH. The amount of alkali metal hydroxide which may be used, on the basis of a molar ratio of alkali metal hydroxide to dihydroperoxide present in the oxidate, ranges from about 0.5/1 to about 5/1. The preferred molar ratio is from about 2/1 to about 2.5/1.

It has been discovered that when alkali metal hydroxide of this high concentration is mixed with an oxidate material that the di-alkali metal salt of dihydroperoxide will precipitate as a solid from the mixture and that the monohydroperoxide, carbinol hydroperoxide, and their alkali metal salts will remain in solution in the liquid oxidate material. Even when excess alkali metal hydroxide is added over the stoichiometric amount necessary to convert all the dihydroperoxide to the sodium salt, the salts of the other oxidation products do not precipitate from the liquid oxidate material. The alkali metal hydroxide is brought into contact with the oxidate material under conditions where sufficient agitation is provided to efficiently mix and stir the reactants. The agitation should be maintained for a period of time sufficinet to allow substantialy all the dihydroperoxide to react with the alkali metal hydroxide. The reaction of the hydroperoxide with the alkali metal hydroxide evolves a substantial amount of heat. Adequate cooling means for removing this heat of reaction should be provided in order to prevent loss of hydroperoxides. Cooling means are generally not required, however, when only small amounts of the reactants are involved, although the rate of addition should be controlled to avoid overheating the mixture. Temperatures in excess of 130° C. should be avoided because of the instability of the hydroperoxides, and also it is advantageous to keep the reaction mixture below the boiling point of the organic solvent in the oxidate mixture to prevent undue loss of such solvent. After all the alkali metal hydroxide solution has been added to the oxidate material, it is allowed to cool to room temperature (about 25° C. or less). If the reaction mixture is subjected to solid-liquid separation at an elevated temerature, substantial amounts of the dihydroperoxide salt will remain in solution with the liquid oxidate material and will not be recovered. Cooling the mixture to about room temperature ensures that most of the dihydroperoxide will precipitate as the alkali metal salt. Any suitable means for cooling the reaction mixture may be employed such as allowing the reaction mixture to stand at room temperature.

Once the reaction mixture has cooled, the alkali metal salts of dihydroperoxide may be recovered by any convenient solid-liquid separation means, for example, by filtration, vacuum filtration, or centrifugal filtration. In this solid-liquid separation step it is sometimes desirable to wash the dihydroperoxide (although not necessary) with a wash liquid which will displace the liquid oxidate material which may be entrained with the solid dihydroperoxide salts. This wash must be able to displace such liquid oxidate materials and at the same time not dissolve and carry off significant amounts of the dihydroperoxide salts. It is convenient to use as a wash liquid the same organic solvent used to dilute the oxidate material because all filtrate material may then be combined and subjected to only one solvent recovery step. However, it is not necessary to use the same material as wash liquid and organic solvent. Many materials may be used as wash liquid, including petroleum ether, benzene, toluene, xylene, diisopropylbenzene, other liquid alkylaromatics, aliphatic hydrocarbons and cyclo aliphatic hydrocarbons. The exact amount of wash liquid required to give the highest dihydroperoxide salt purity with the least dihydroperoxide salt loss depends upon the particular wash liquid selected. A good operable range of wash liquid volumes lies between about 1/4 and about 1 times the volume of oxidate material from which the dihydroperoxide salt is recovered.

A unique feature of the process is that nearly all the water added to the oxidate material in the form of aqueous metal hydroxide remains in the solid dihydroperoxide salts, and very little is removed with the liquid oxidate materials. The absence of water greatly simplifies any further treatment of the liquid oxidate materials before they are recycled to the oxidation reactor.

The liquid oxidate materials may be subjected to further treatment after separation from the solid dihydroperoxide salts. For instance, the organic solvent may be recovered and used to treat additional oxidate materials and the wash may be likewise recovered for reuse. Should the wash liquid and organic solvent be the same material, then the oxidate material filtrate and the wash liquid filtrate may be combined and subjected to the same recovery treatment. The liquid oxidate materials remaining after recovery of the organic solvent and the wash liquid may be returned to the oxidation reaction as a recycle stream or reserved for other treatment or use.

The solid dihydroperoxide salts recovered from the solid-liquid separation step of the present process are of a high degree of purity except for the appreciable amount of water present. These dihydroperoxide salts may be dried, for example, in a vacuum oven, to effect a substantially pure state. Such a drying process may be very carefully undertaken, as these dihydroperoxide salts are very unstable and may decompose rapidly when substantially all the water is removed from them.

Dihydroperoxide may be recovered from the dihydroperoxide salts by a process of acid treating. To accomplish such a dihydroperoxide recovery, the alkali metal salts of the dihydroperoxide are mixed with water in a weight ratio of about 1/1 to about 10/1 water to dihydroperoxide salt. It is not necessary that all the dihydroperoxide salt be in solution. However, sufficient water to dissolve the inorganic salts which form must be present. The mixture of dihydroperoxide and water is treated with a weak acid, such as $CO_2$, acetic and or other carboxylic acid, or dilute mineral acids, to a pH from about 11 to about 7.0 for a time sufficient for the alkali metal salts of the dihydroperoxide to substantially react with the acid to form dihydroperoxide and alkali metal salts of the acid. The dihydroperoxides are substantially insoluble in water, therefore they separate from the water solution and may be easily recovered therefrom by a physical separation means. As stated above, sufficient water should be present to maintain the inorganic salts in solution. By following this method, dihydroperoxides of a high degree of purity may be recovered in good yield.

Another method of recovering the dihydroperoxides from the acid treated water mixture comprises the addition of a water immiscible organic liquid, in which the dihydroperoxide salts are insoluble and the dihydroperoxide is soluble, to the water mixture during the acidification reaction in sufficient amounts to dissolve the dihydroperoxide which forms. Weight ratios of organic liquid to alkali metal salts of the dihydroperoxide from about 1/1 to about 10/1 are sufficient. Thus, the dihydroperoxides may be recovered in a high purity and good yield from the organic liquid by such methods as crystallization of the dihydroperoxide or vaporization of the organic liquid.

The dihydroperoxide may also be recovered from it alkali metal salts by extracting an aqueous solution of the alkali metal salt with an extraction liquid selected from water-immiscible aliphatic ketones, ethers, alcohols and chlorinated hydrocarbons at temperatures between 70–100° C. and in a ratio of extraction liquid to aqueous phase of 0.2—5:1, thereby extracting the dihydroperoxide into the organic phase. The dihydroperoxide may conveniently be recovered from the organic extraction liquid by such methods as cystallization, or solvent vaporization.

To further describe and to specifically illustrate the present invention, the following examples are presented. These examples are not to be construed in any manner as limiting the conditions, application or objects of the present invention.

EXAMPLE I

In this experiment, m-diisopropylbenzene dihydroperoxide was separated from the oxidate resulting from the oxidation of m-diisopropylbenzene with molecular oxygen in the presence of aqueous sodium carbonate. A 200 gm. sample of the oxidate, free of the aqeuous phase, contained 34.2 gm. m-diisopropylbenzene dihydroperoxide, 78.0 gm. m-diisopropylbenzene monohydroperoxide and 8.96 gm. meta-(2-hydroperoxy-2-propyl) phenyldimethylcarbinol. To the 200 gm. sample of oxidate, 200 gm. of benzene was added. This oxidate-benzene solution was placed in an open, stirred vessel where 55.7 gm. of an aqueous solution containing 28.3 gm. NaOH (50.8% NaOH) was added dropwise. This amounted to 4.68 moles NaOH per mole m-diisopropylbenzene dihydroperoxide. During the addition of the NaOH, the temperature of the solution rose to 50° C. and was allowed to cool on standing to 25° C. after all the NaOH was added. Upon cooling, a solid material precipitated from the solution. No water phase was present in the system. The cooled mixture was filtered through a medium frit sintered glass filter, employing slight vacuum, and the filter cake was washed with 100 gm. benzene. The cake wash and the filtrate were combined and analyzed. THe results of this analysis are as follows.

TABLE 1

|  | Oxidate gm. | NaOH Solution gm. | Filtrate gm. | Filter Cake gm. | Filter Cake % Yield |
|---|---|---|---|---|---|
| dihydroperoxide | 34.2 | — | 1.92 | 30.86 | 90.23 |
| monohydroperoxide | 78.0 | — | 69.9 | 1.21 | — |
| carbinol hydroperoxide | 8.96 | — | 5.07 | 0.563 | — |
| sodium hydroxide | — | 28.3 | 13.53 | 11.47 | — |

From the above data it can be observed that even though a stoichiometric excess of NaOH was employed (based upon two moles of NaOH per mole of m-diisopropylbenzene dihydroperoxide), most of the monohydroperoxide remained in the benzene-oxidate solution and that most (90.23%) of the dihydroperoxide precipitated as a solid from the oxidate-benzene solution. The method of this example produces the sodium salt of m-diisopropylbenzene dihydroperoxide of high purity in good yield from an oxidate solution containing the m-diisopropylbenzene dihydroperoxide in a minor amount.

EXAMPLE II

In this experiment m-diisopropylbenzene dihydroperoxide was separated from a sample of the same oxidate as was employed in Example I. However, only the stoichiometric amount of NaOH necessary to convert the dihydroperoxide to the disodium salt was employed. To 1000 gm. of the oxidate, 1000 gm benzene was added to reduce the viscosity. Then to the oxidate-benzene solution 119 gm. of 50.8% NaOH solution was slowly added with constant stirring. The mixture temperature rose to 42° C. and after all the NaOH was added, the mixture was allowed to cool to 25° C. On cooling, a solid precipitated from the oxidate-benzene solution. No water phase separated from the mixture. The solids were separated from the mixture by filtration through a course frit sintered glass filter employing light vacuum. These solids were suspended in 250 gm. of benzene, filtered through a course frit sintered glass filter, and the filter cake was washed with 250 gm. of benzene. The recovered dihydroperoxide salt cake weighed 293.1 gm. The weight distribution of dihyroperoxide, monohydroperoxide and carbinol hydroperoxide are given for the solid cake, the filtrate and the combined benzene wash liquors as shown in Table II.

TABLE II

|  | Oxidate gm. | NaOH gm. | Filtrate gm. | Benzene Washes Combined gm. | Filter Cake gm. |
|---|---|---|---|---|---|
| dihydroperoxide | 171.0 | — | 17.34 | 0.94 | 151.5* |
| monohydroperoxide | 390.0 | — | 326.6 | 38.09 | 1.64 |
| carbinol hydroperoxide | 44.8 | — | 38.70 | 3.50 | 4.72 |
| sodium hydroxide | — | 60.45 | 1.55 | 0.12 | 52.65 |

*Note:
The dihydroperoxide recovered in the filter cake is 88.6% of that present in the oxidate.

The results of these analyses indicate that 88.6% of the dihydroperoxide was recovered in the solid filter cake, also most of the monohydroperoxide and the m-(2-hydroperoxy-2-propyl) phenyldimethyl carbinol remained in the liquid filtrate. The yield of dihydroperoxide in this example is substantially equal to the yield obtained in Example I where a large excess of NaOH was employed.

EXAMPLE III

The method of Examples I and II was repeated except only 0.66 of the stoichiometric amount of NaOH necessary to convert all the dihydroperoxide to the disodium salt was employed. An analysis of the solid filter cake obtained showed that 58.2% of the dihyroperoxide present in the oxidate was recovered in the filter cake.

These experiments indicate that a high proportion of the NaOH added to the mixture reacts to form the disodium salt of the dihyroperoxide. This salt precipitates from the oxidate solution while nearly all the monohydroperoxide remains in solution, even when a large excess of NaOH is employed. This is a surprising result, as the prior art teaches that the monohydroperoxide may be separated from the oxidate solution by employing concentrated solutions of NaOH. Another surprising result of these experiments is the absence of an aqueous phase. The water present does not separate to form a liquid phase separate from the oxidate-benzene liquid phase but is included in the solid disodium salt of the dihydroperoxide. This absence of a water phase simplifies the separation of the liquid and solid phases and allows most of the sodium salt of the monohydroperoxide to remain in solution in the oxidate-benzene solution.

EXAMPLE IV

In this experiment, a benzene-moist cake of the sodium salt of m-diisopropylbenzene dihydroperoxide produced by the method of Example (II) was treated with carbon dioxide to recover the m-diisopropylbenzene dihydroperoxide from said sodium salt.

The sodium salt of m-diisopropylbenzene dihydroperoxide was found by analysis to comprise 70.58 wt% of a solid cake produced according to the process of Example II. A sample of this cake, weighing 1229 gm., was placed into a large beaker containing 1604 gm deionized water and 1704 gm. benzene. The 1604 gm. of water was sufficient to dissolve all the sodium carbonate produced as a result of carbon dioxide treament of the dihydroperoxide sodium salt. The 1704 gm. of benzene was sufficient to dissolve all the m-diisopropylbenzene dihydroperoxide produced.

The beaker containing the salt-benzene-water mixture was fitted with a magnetic stirring bar and pH measuring electrodes. Carbon dioxide gas was admitted into the mixture through a glass tube with constant stirring. The pH of the mixture was monitored continuously during the carbon dioxide treatment. Upon reaching a pH reading of 11.90 on the pH meter the carbon dioxide flow was stopped, mixing was stopped and the aqueous layer was allowed to separate from the benzene layer. The benzene layer, containing the m-diisopropylbenzene dihydroperoxide was separated in a separatory funnel from the aqueous layer. The separated benzene layer was mixed with 90 ml deionized water and was treated with carbon dioxide until the pH of the mixture registered 7.60 on the pH meter. This benzene layer was separated from the aqueous layer in a separatory funnel and was treated with anhydrous $Na_2SO_4$ to give a clear benzene solution of m-diisopropylbenzene dihydroperoxide. An analysis of this dried benzene solution indicated that it contained 95% of the theoretical amount of m-diisopropylbenzene dihydroperoxide present in the original cake. This dried benzene solution of m-diisopropylbenzene dihydroperoxide was transferred to a distillation flask fitted with a water-cooled condenser. An amount of hexane was added to the benzene solution and this mixture was brought to its boiling point. Additional hexane was added to the boiling mixture until a permanent turbidity developed. This mixture was then cooled with constant stirring to room temperature. The cooled mixture was seeded with a small amount of m-diisopropylbenzene dihydroperoxide and crystallization occurred. The crystalline product was separated from the liquid by filtration and was dried over night in a vacuum oven. The dried crystalline product was analyzed as 96.98% m-diisopropylbenzene dihydroperoxide. The m-diisopropylbenzene dihydroperoxide recovered in crystalline form amounted to 79.6% of the dihydroperoxide present in the water-dried benzene solution. Thus 75.6% of the total theoretical amount of m-diisopropylbenzene dihydroperoxide present in the beginning sample was recovered by this method.

EXAMPLE V

In this example, the diisopropylbenzene dihydroperoxide was recovered from an oxidate similar to that used in Example I by treating the oxidate with sodium hydroxide pellets of 98.9% purity.

200 grams of benzene, 22.22 grams sodium hydroxide pellets (22.09 g NaOH), and 200 grams oxidate (34.2 grams meta-diisopropylbenzene dihydroperoxide) were mixed together at room temperature in a 600 ml beaker. This mixture was slowly heated, with constant mixing. At about 70° C. the sodium hydroxide pellets disintegrated and dissolved. At about 80° C. the mixture gently boiled. Upon boiling, the mixture was removed from the heat source and allowed to cool to 25° C. The cooled mixture, containing a solid precipitate, was then vacuum filtered through a medium frit sintered glass filter. The filter cake was drawn by vacuum filtration employing a rubber dam to cover the filter cake. This cake was resuspended in 50 gm. benzene and refiltered through the medium frit filter and was subsequently washed with 50 gm. benzene. This last cake was air dried over night to yield 51 grams net weight. Substantial losses of solids were experienced due to handling.

The filtrates and wash liquors were combined, along with the benzene used to wash out the equipment, to yield 387 grams, net, of liquid. An analysis of these materials showed the following results:

|  | Oxidate gms | Filtrate gms | Filter Cake gms | Recovery % |
|---|---|---|---|---|
| dihydroperoxide | 34.2 | 2.36 | 21.4 | 62.6 |

The low recovery percentage is accounted for by handling losses in transferring the solid from one piece of equipment to another.

The filter cake was also analyzed, showing these results:

| dihydroperoxide | 21.4 gm |
|---|---|
| monohydroperoxide | 2.73 gm |
| carbinol hydroperoxide | 0.92 gm |
| benzene (by difference) | 25.95 gm |

This yields a dihydroperoxide of 85.4% purity on a benzene-free basis.

The examples included herein are intended to demonstrate the operation of my invention and are not to be construed as in any way limiting the scope of said invention. And, while I have described my invention herein with a certain degree of particularity, it should be understood that the scope of my invention should not be limited thereto but should be afforded to full breadth of the appended claims.

I claim:

1. A method for recovering dialkylbenzene dihydroperoxide from an oxidation reaction product containing dialkylbenzene dihydroperoxide, dialkylbenzene monohydroperoxide, and unreacted dialkylbenzene, comprising the steps:
   (a) mixing said oxidation reaction product with an amount of water immiscible organic solvent in a volume ratio of organic solvent to reaction product of about 0.1/1 to about 6/1, said organic solvent being of a type which is substantially non-reactive, under the processing conditions, with said reaction product or alkali metal hydroxide and in which alkali metal salts of diakylbenzene dihydroperoxides are substantially insoluble;
   (b) treating, at a temperature maintained below about 130° C., the oxidation reaction product-solvent mixture with alkali metal hydroxide in a molar ratio of hydroxide to dihydroperoxide of about 0.5/1 to about 5/1 to precipitate the alkali metal salt of the dialkylbenzene dihydroperoxide from said solution,
(c) separating the solid alkali metal salt of the dihydroperoxide from the solution, and
(d) converting the dihydroperoxide salt to dialkylbenzene dihydroperoxide.

2. The method of claim 1 including:
(a) treating the dialkylbenzene dihydroperoxide salt with water in a weight ratio of water to dihydroperoxide of from about 1/1 to about 10/1, and
(b) adjusting the Ph of the water-salt mixture to a value between about 11 and about 7 by treating said mixture with an acid selected from the group consisting of carbon dioxide, carboxylic acids, and dilute mineral acids, thereby causing dialkylbenzene dihydroperoxide to separate from the water phase, and
(c) recovering the separated dialkylbenzene dihydroperoxide from the acid treated mixture.

3. The method of claim 1 wherein the water immiscible organic solvent is selected from the group consisting of benzene, liquid monoethylbenzenes, liquid dialkylbenzenes; $C_3$–$C_{12}$ aliphatic hydrocarbons, liquid chlorinated aromatic hydrocarbons and mixtures thereof.

4. The method of claim 1 wherein the organic solvent is benzene.

5. The method of claim 1 wherein the alkali metal hydroxide is sodium hydroxide.

6. The method of claim 1 wherein the alkali metal hydroxide is added as an aqueous solution having a concentration of from about 40 to about 100% by weight.

7. The method of claim 1 wherein said mixture of oxidation reaction product-organic solvent-alkali metal hydroxide is cooled to a temperature of about 25° C. or less before separation of said alkali metal salt of dialkylbenzene dihydroperoxide.

8. A method for recovering diisopropylbenzene dihydroperoxide from an oxidation reaction product which contains said diisopropylbenzene dihydroperoxide, diisopropylbenzene monohydroperoxide in an amount of about 2 to 3 times the amount of said diisopropylbenzene dihydroperoxide, (2-hydroperoxy-2-propyl) phenyl dimethyl carbinol, and unreacted diisopropylbenzene, comprising the steps:
(a) mixing said oxidation reaction product with a water immiscible organic solvent in a volume ratio of solvent to oxidation reaction product of between about 0.1/1 to about 6/1 to form a reaction product-solvent mixture, said organic solvent being of a type which is substantially non-reactive, under the processing conditions, with said reaction product or alkali metal hydroxide and in which alkali metal salts of dialkylbenzene dihydroperoxides are substantially insoluble,
(b) treating, at a temperature maintained below about 130° C., the oxidate-solvent solution with alkali metal hydroxide in a molar ratio of alkali metal hydroxide to diisopropylbenzene dihydroperoxide of between about 0.5/1 to 5/1 to precipitate the alkali metal salt of said diisopropylbenzene dihydroperoxide from said solution,
(c) recovering said precipitated solid alkali metal salt of said diisopropylbenzene dihydroperoxide substantially free of diisopropylbenzene monohydroperoxide and (2-hydroperoxy-2-propyl) phenyl dimethyl carbinol,
(d) redissolving said alkali metal salt in an aqueous solution, and
(e) recovering diisopropylbenzene dihydroperoxide from said aqueous alkali metal salt solution.

9. The method of claim 8 wherein the organic solvent is selected from the group consisting of benzene, liquid monoethylbenzenes, liquid dialkylbenzenes; $C_3$–$C_{12}$ aliphatic hydrocarbons, liquid chlorinated aromatic hydrocarbons and mixtures thereof.

10. The method of claim 8 wherein the organic solvent is benzene.

11. The method of claim 8 wherein the alkali metal hydroxide is sodium hydroxide.

12. The method of claim 8 wherein the alkali metal hydroxide is added as an aqueous solution having a concentration of from about 40 to about 100% by weight.

13. The method of claim 8 wherein the mixture of said reaction product-organic solvent-alkali metal hydroxide is cooled to a temperature of about 25° C. or less before separation of said precipitated alkali metal salt of diisopropylbenzene dihydroperoxide.

14. A method for recovering diisopropylbenzene dihydroperoxide, as its alkali metal salts, from an oxidate which contains diisopropylbenzene dihydroperoxide, diisopropylbenzene monohydroperoxide in an amount of about 2 to about 3 times the amount of said dihydroperoxide, unreacted diisopropylbenzene, and (2-hydroperoxy-2-propyl) phenyl carbinol, comprising the steps:
(a) treating said oxidate with a water immiscible organic solvent in a volume ratio of solvent to oxidate of about 0.1/1 to about 6/1 to form an oxidate-solvent solution, said organic solvent being of a type which is substantially non-reactive, under the processing conditions, with said oxidate or alkali metal hydroxide and in which alkali metal salts of dialkylbenzene dihyroperoxides are substantially insoluble,
(b) treating, at a temperature maintained below about 130° C., the oxidate-solvent solution with alkali metal hydroxide in a molar ratio of alkali metal hydroxide to diisopropylbenzene dihydroperoxide of about 0.5/1 to about 5/1, thereby precipitating the alkali metal salt of said dihydroperoxide from said solution,
(c) receiving said precipitated, solid, alkali metal salt of the diisopropylbenzene monohydroperoxide substantially free of diisopropylbenzene monohydroperoxide and (2-hydroperoxy-2-propyl) phenyl carbinol.

15. The method of claim 13 wherein the recovered solid alkali metal salt of diisopropylbenzene dihydroperoxide is treated with a drying means to remove substantially all the water present in the salt, thereby yielding said salt in a high degree of purity.

16. The method of claim 14 wherein the alkali metal hydroxide is added as an aqueous solution having a concentration of from about 40 to about 100% by weight.

* * * * *

UNITED STATES PATENT OFFICE
CERTIFICATE OF CORRECTION

PATENT NO. : 4,230,890
DATED : October 28, 1980
INVENTOR(S) : Ward J. Burkholder It is certified that error appears in the above-identified patent and that said Letters Patent are hereby corrected as shown below:

1. Column 6, Line 1, "174" should be --1/4--.

Signed and Sealed this

Fifth Day of May 1981

[SEAL]

Attest:

RENE D. TEGTMEYER

Attesting Officer     Acting Commissioner of Patents and Trademarks